United States Patent [19]

Schmitz

[11] Patent Number: 5,459,262
[45] Date of Patent: Oct. 17, 1995

[54] PROCESS FOR THE PREPARATION OF PHENYLBENZAMIDE DERIVATIVES

[75] Inventor: Christian Schmitz, Anse, France

[73] Assignee: Rhone-Poulenc Agrochimie, Lyon Cedex, France

[21] Appl. No.: 193,458

[22] Filed: Feb. 8, 1994

[30] Foreign Application Priority Data

Feb. 8, 1993 [FR] France .................. 93 01558

[51] Int. Cl.[6] .................. C07C 231/12; C07D 295/192
[52] U.S. Cl. .................. 544/174; 564/169; 564/171
[58] Field of Search .................. 544/174; 564/171

[56] References Cited

FOREIGN PATENT DOCUMENTS 0360701  3/1990  European Pat. Off. .

OTHER PUBLICATIONS

Das et al, J. Chem. Soc., Dalton Trans. (JCDTBI), 7, pp. 662–664 (1977).
Das et al, Australian Journal of Chemistry, vol. 27, pp. 1177–1183 (1974).

*Primary Examiner*—Robert W. Ramsuer
*Attorney, Agent, or Firm*—Burns, Doane, Swecker & Mathis

[57] ABSTRACT

A new process for the preparation of a phenylbenzamide derivative of the formula

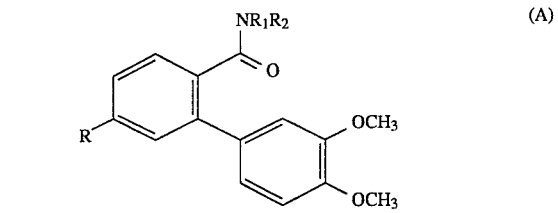

wherein R is $C_1$–$C_2$ alkyl, substituted with 2 to 5 F, and each of $R_1$ and $R_2$, which can be identical or different, is methyl or ethyl, or —$NR_1R_2$ is morpholino, comprising condensing a haloenone (I) with an acetoamide (II), according to scheme

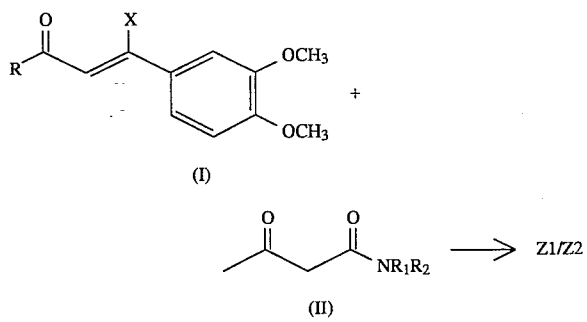

in the presence of an organic solvent and 1 to 2 equivalents of base, followed by converting the resulting product in two steps, one of which is a reduction, to the corresponding compound of formula (A). Phenylbenzamides of formula (A) are agricultural fungicides. The new process is suited to large-scale production of these compounds.

7 Claims, No Drawings

PROCESS FOR THE PREPARATION OF PHENYLBENZAMIDE DERIVATIVES

The subject of the present invention is a new process for the preparation of phenylbenzamide derivatives.

It is known, particularly according to European Patent Publication No. 0360701, that some of these compounds exhibit interesting fungicidal properties. EP 0360701 describes, in addition to the properties of these products, a process for their preparation. Such a process gives satisfactory yields at the laboratory stage. However, its performance is insufficient for industrial production. Furthermore, some steps, such as the biaryl coupling, which use expensive catalysts such as those based on precious metals or organometallics, are costly. Other steps, such as the diazotizations, are dangerous. It is therefore necessary to find a new route which is more suited to large-scale production.

The present invention relates to a process which presents none of the above disadvantages. More particularly, its subject is a process for the preparation of compounds of formula A,

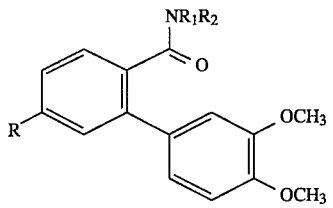

in which R is an alkyl containing 1 to 2 carbon atoms, substituted with 2 to 5 fluorine atoms, $R_1$ and $R_2$, which may be identical or different, are each methyl or ethyl, or together with the adjacent nitrogen atom form a morpholino radical, characterized in that a condensation of a haloenone of formula I, in which R has the same meaning as above, is carried out with an acetoamide of formula II, in which $R_1$ and $R_2$ have the same meanings as above according to the scheme:

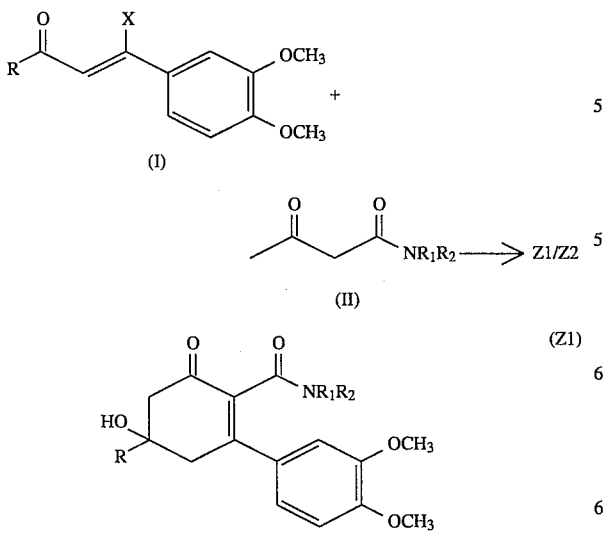

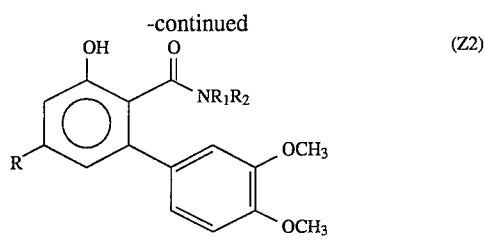

in the presence of an organic solvent and 1 to 2 equivalents of base, and in that the resulting product is subjected to a conversion in two steps, one of which is a reduction.

The molar ratio Z1/Z2 depends on the quantity of base used, Z1 only being obtained for a quantity of one equivalents of base, Z2 only being obtained for a quantity of two equivalents of base, a mixture Z1/Z2 being obtained for a quantity of base which is intermediate between one and two equivalents, the ratio varying as a function of the duration of the reaction and the temperature.

Among the very many "base-solvent" couples which are possible for carrying out this condensation, an aliphatic alcohol such as ethanol and an inorganic base, in a stoichiometric amount, derived from an alkali metal or an alkaline-earth metal, such as baryta are advantageously used. In practice, when the haloenone is a chloroenone, the latter is placed in solution with the acetoacetamide (1-1.1 equivalent) in absolute ethanol at a temperature between 10° C. and 30° C. and then treated with the base (1-1.1 equivalent), which may be added several times as appropriate. When all the chloroenone has reacted, the reaction mixture is gradually heated to reflux to complete the reaction (6–48 hours). The cooled reaction mixture is filtered, then concentrated; the residue is crystallized from a solvent such as ethyl acetate.

The acetoacetamides II are known products, and very often on the market. They may be prepared according to one of two routes described in the literature: according to the first, diketene is reacted with an amine $HNR_1R_2$ (*Chemical Reviews* 1986 vol. 86, p. 241); according to the second, a transamidation of a commercially available alkyl acetoacetate is carried out, preferably t-butyl acetoacetate, which is more reactive than methyl or ethyl acetoacetate (*Journal Organic Chemistry*), using an amine $HNR_1R_2$.

The haloenone compounds I are new products which may be obtained, in a manner known per se, by halogenation of the corresponding diones of formula V, according to the scheme:

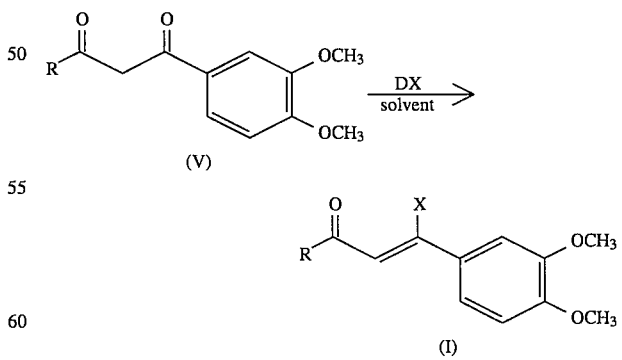

in which R has the same meaning as in the formula of the compound A and DX is a halogenating agent, the labile part of which is X.

The reaction is carried out in an inert solvent medium, at a temperature between 40° C. and reflux.

By way of inert solvent, there may preferably be used an aromatic solvent such as toluene, in an aprotic dipolar solvent such as N,N-dimethylformamide or in the halogenating agent itself if this latter is liquid. By way of halogenating agent, there may be used thionyl chloride, phosphorus pentachloride, trichloride or oxychloride, oxalyl chloride or phosgene. In practice, the dione of formula V is run into a suspension or a solution of halogenating agent (1 to 2 equivalents) in the chosen solvent at a temperature between 0° C. and the reflux temperature of the reaction mixture. When the addition has ended, the reaction mixture is heated to a temperature between 20° C. and the reflux temperature of the reaction mixture to end the reaction. The mixture is hydrolysed with water and the reaction product is isolated by standard methods and optionally purified by recrystallization.

The diones of formula V are new products which also form part of the invention and may be obtained by reaction of a fluoroacetic ester with an acetophenone in an anhydrous solvent, in the presence of a nonaqueous base, according to the scheme:

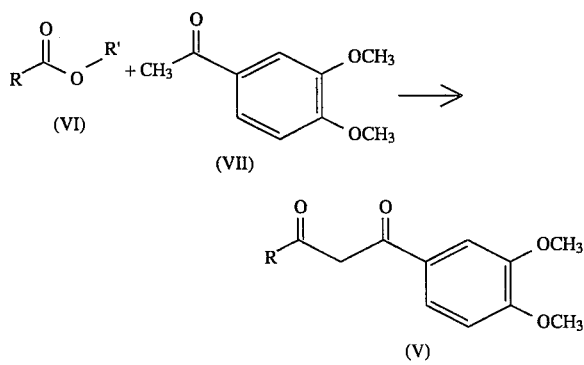

in which R is an alkyl containing 1 to 2 carbon atoms, substituted with 2 to 5 fluorine atoms and R' is an alkyl containing 1 to 4 carbon atoms.

According to a first variation, the condensation of the haloenone I with the acetoamide II is carried out in the presence to a stoichiometric amount of base with production of the compound Z1, which is successively subjected to:

a) a reduction, to give the compound III according to the scheme:

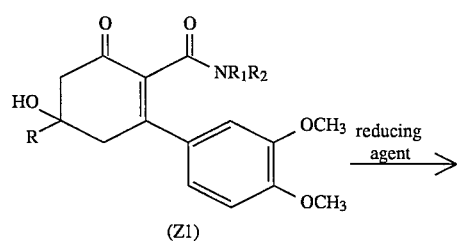

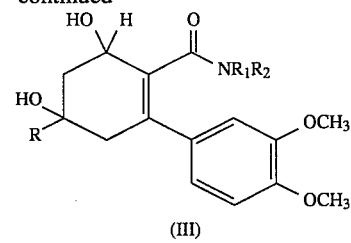

in which R, $R_1$ and $R_2$ have the same meanings as for the compound Z1, in the presence of a reducing agent, in solvent medium, and that b) the compound III is next subjected to an aromatization according to the scheme:

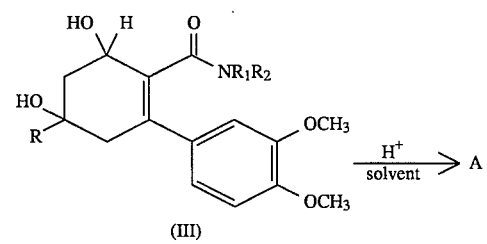

by heating to a temperature between 50° and 120° C., in anhydrous solvent medium, in the presence of traces of strong acid.

The reduction reaction is carried out in the presence of a reducing agent, in a solvent medium. The solvent may be, for example, an aliphatic alcohol such as ethanol or methanol, or an aliphatic ether such as tetrahydrofuran or a mixture of several of these solvents. As a reducing agent, a mixed hydride of an alkali metal such as, for example, sodium or potassium borohydride, is preferably used.

In practice, the hydroxycyclohexenone is suspended in the chosen solvent and then treated at a temperature between 0° C. and room temperature with an aqueous or alcoholic solution of the chosen reducing agent. When all the hydroxycyclohexenone has reacted, the solvent is evaporated under reduced pressure and the mixture is treated with water, extracted using an organic solvent, dried and then evaporated to obtain a residue which consists of a mixture of two diastereoisomers, which it is unnecessary to separate for the following step. These products are fairly difficult to crystallize.

The aromatization reaction is carried out by heating the above diol in an anhydrous solvent which may be an aromatic hydrocarbon such as toluene, in the presence of traces of strong inorganic or organic acids such as sulphuric or p-toluenesulphonic acid, and by entraining the water formed in a continuous fashion.

When the reaction has ended, the solvent is evaporated and the product is isolated by standard methods and optionally purified by recrystallization.

According to a second variation, condensation of the haloenone I with the acetoamide II is carried out in the presence of a quantity of base which is twice the stoichiometry, with production of the compound Z2, which is successively subjected to:

a) an activation reaction with an activating agent VI, to give a new product IV, which forms part of the invention, according to the scheme:

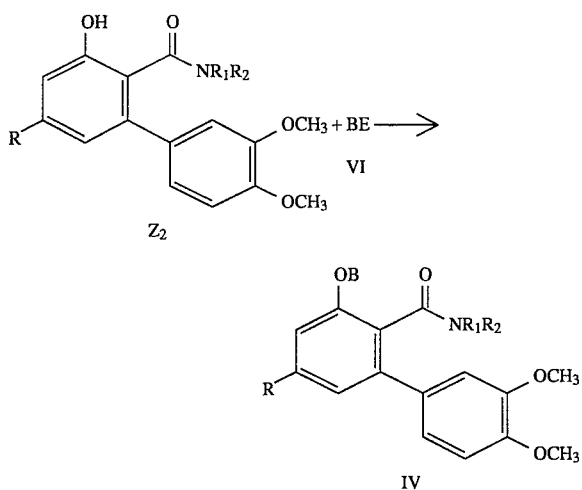

in which R, $R_1$ and $R_2$ have the same meaning as in Z2 and the activating agent BE, in which B is the part which attaches to the hydroxyl and E is a residue, is chosen from the group comprising cyanuric chloride, 5-chloro-2-phenyl-tetrazole, optionally halogenated alkylsulphonyl chlorides and anhydrides, saccharin chloride and sulphur trioxide, b) reduction of the compound IV to compound A, using hydrogen gas in the presence of a conventional hydrogenation catalyst, according to the scheme:

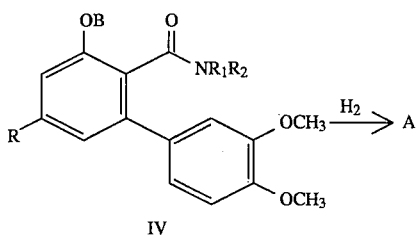

As catalyst, palladium on charcoal or Raney nickel may be mentioned by way of example.

As new compounds, the invention also concerns the compounds I, Z1, Z2, III, IV and V, which may be used as intermediates for the production of compound A.

The invention also concerns a process for the preparation of compound Z2, characterized in that Z1 is treated with a base in an organic solvent medium.

The following examples are given to illustrate the process according to the invention, without limiting it.

Example 1

1-(3,4-dimethoxyphenyl)-4,4,4-trifluoro-1,3-butanedione

216 g (4 mol) of anhydrous sodium methylate and 3.5 l of toluene are introduced into a 10 liter round-bottomed flask and, under vigorous stirring, 705 g (5 mol) of ethyl trifluoroacetate are then run in; the temperature rises slowly to 30° C. After cooling in an ice bath, a solution of 720 g (4 mol) of 3,4-dimethoxyacetophenone in 0.5 l of toluene is added dropwise to the reaction mixture; a white precipitate slowly forms. The mixture is next left stirred overnight and then heated to 50° C. for three hours. After cooling, 2 l of water and 330 ml of concentrated hydrochloric acid are added, the organic phase is separated off after settling has taken place, dried over magnesium sulphate, filtered and evaporated to obtain 1060 g (96%) of a yellow solid melting at 87°–89° C.

In the same way:

1-(3,4-dimethoxyphenyl)-4,4,5,5,5-pentafluoro-1,3-pentanedione melting at 72° C. was obtained.

Example 2

(cis) 4-chloro-4-(3,4-dimethoxyphenyl)-1,1,1-trifluoro-3-buten-2-one 1187 g (5.7 mol) of phosphorus pentachloride and 5 l of anhydrous toluene are introduced into a 20 liter round-bottomed flask, the mixture is cooled and then 1060 g (3.8 mol) of 1-(3,4-dimethoxyphenyl)-4,4,4-trifluro-1,3-butanedione dissolved in 4 l of toluene are rapidly run in. The reaction mixture is rapidly brought to 60° C. and then maintained at this temperature for 2 hours. The reaction mixture is poured into 10 l of water and 5 kg of ice, extracted with 5 l of ethyl acetate, washed with dilute sodium hydroxide, dried over sodium sulphate, filtered and evaporated to give 1132 g of a dark brown solid. The crude product is recrystallized from 3 l of ethanol to give 741 g (yield: 67%) of a lemon-yellow solid melting at 98°–100° C.

In the same way:
(Z) 5-chloro-5-(3,4-dimethoxyphenyl)-1,1,1,2,2-pentafluro-4-penten-3-one melting at 67° C. was obtained.

Example 3

N-ethyl-N-methyl acetoacetamide

Into a 1 l stainless steel autoclave are introduced 158 g (1 mol) of tert-butyl acetoacetate and 61 g of N-ethyl-N-methylamine (1.05) mol), followed by heating at 130° C. for 6 hours; the pressure does not exceed 10 bars. The contents of the autoclave are transferred to a round-bottomed flask and the tert-butanol formed is evaporated under reduced pressure to give 140 g (98%) of N-ethyl-N-methylacetoacetamide which is sufficiently pure to be used in the following reaction.

The other acetoacetamides are commercially available.

Example 4

N,N-diethyl-1-carboxamide-4-trifluoromethyl-4-hydroxy-6-(3,4-dimethoxyphenyl)cyclohex-6-en-2-one 2800 g (9.5 mol) of 4-chloro-4-(3,4-dimethoxy-phenyl)-1,1,1-trifluoro-3-buten-2-one and 4.5 l of anhydrous ethanol are added to a 10 liter round-bottomed flask and then 1790 g (11.4 mol) of N,N-diethyl acetoacetamide are rapidly run in. A total of 1670 g (5.3 mol) of bariumhydroxide hydrate $Ba(OH)_2.8H_2O$ are then added in five portions at 2-hourly intervals at room temperature with constant stirring. After stirring overnight, the reaction mixture is slowly brought to reflux, then maintained at this temperature for 6 hours. The reaction mixture is filtered through diatomaceous earth, and washed with 2.5 l of cold ethanol and 2.5 l of cold ethyl acetate. The white solid thus obtained is dried at 50° C. under reduced pressure to give 2548 g (64.6%) of a white solid melting at 174° C.

The following derivatives are obtained in the same way:
N-ethyl-N-methyl-1-carboxamide-4-trifluoromethyl-4-hydroxy-6-(3,4-dimethoxyphenyl)cyclohex-6-en-2-one melting at 163°–165° C.,
1-(4-morpholino)carbonyl-4-trifluoromethyl-4-hydroxy-6-(3,4-dimethoxyphenyl)cyclohex-6-en-2-one melting at 183° C., N-ethyl-N-methyl-1-carboxamide-4-(1,1,1,2,2 -pentafluoroethyl)-4-hydroxy-6-(3,4-dimethoxyphenyl)cyclohex-6-en-2-one melting at 163° C.,
N,N-diethyl-1-carboxamide-4-(1,1,1,2,2-penta-fluoroethyl)- 4-hydroxy-6-(3,4-dimethoxyphenyl)cyclohex-6 -en-2-one melting at 174°–176° C.

Example 5

N,N-diethyl-1-carboxamide-4-trifluoromethyl-6 -(3,4-dimethoxyphenyl)cyclohex-6-ene-2,4-diol 1388 g (3.31 mol) of N,N-diethyl-1-carboxamide-4 -trifluoromethyl-4-hydroxy-6-(3,4-dimethoxyphenyl)cyclohex-6-en-2-one and 12 l of anhydrous methanol are introduced into a 20 liter round-bottomed flask. A solution of 146 g (3.82 mol) of sodium borohydride in 1500 ml of iced water is then rapidly run into the reaction mixture, which is cooled to 0° C., with constant stirring. When the addition has ended, the mixture is allowed to return to room temperature and left stirring for 3 hours. The medium is next filtered through diatomaceous earth and then evaporated under reduced pressure. The residue is taken up with water, extracted with dichloromethane, washed with water and then evaporated under reduced pressure to give 1322 g (yield: 95.2 %) of a faintly coloured oil which crystallizes slowly. The product thus obtained is used as is for the following step.

The following derivatives were obtained in the same way:
N-ethyl-N-methyl-1-carboxamide-4-trifluoromethyl-6-(3,4-dimethoxyphenyl)cyclohex-6-ene-2,4-diol,
1-(4-morpholino)carbonyl-4-trifluoromethyl-6-(3,4-dimethoxyphenyl)cyclohex-6-ene-2,4-diol,
N-ethyl-N-methyl-1-carboxamide-4-(1,1,1,2,2 -pentafluoroethyl)-6-(3,4-dimethoxyphenyl)cyclohex-6-ene-2,4-diol,
N,N-diethyl-1-carboxamide-4-(1,1,1,2,2-pentafluoroethyl)-6-(3,4-dimethoxyphenyl)cyclohex-6-ene-2,4-diol.

Example 6

N,N-diethyl-4-trifluoromethyl-2-(3,4-dimethoxyphenyl)benzamide 2429 g (5.82 mol) of N,N-diethyl-1-carboxamide-4 -trifluoromethyl-6-(3,4-dimethoxyphenyl)cyclohex-6-ene-2,4-diol, 13 l of anhydrous toluene and 118 g of p-toluenesulphonic acid monohydrate are introduced into a 20 liter round-bottomed flask. The reaction mixture is brought to reflux while continuously removing water formed using a Dean and Stark apparatus. The reaction has ended when no more water is formed; the reaction mixture is then filtered through diatomaceous earth and evaporated under reduced pressure. The residue is taken up in water, extracted with dichloromethane, washed with water and then evaporated under reduced pressure to give 2175 g (yield: 98%) of a faintly coloured oil which crystallizes slowly. The product thus obtained may be purified by recrystallization from a mixture of isopropyl ether and pentane, to give a white solid melting at 108°– 110° C.

The following derivatives were obtained in the same way:
N-ethyl-N-methyl-4-trifluoromethyl-2-(3,4-dimethoxyphenyl)benzamide melting at 103°–105° C.,
1-(4-morpholino)carbonyl-4-trifluoromethyl-2-(3,4-dimethoxyphenyl)benzene melting at 183°–185° C.,
N-ethyl-N-methyl-4-(1,1,1,2,2-pentafluoroethyl)-2-(3,4-dimethoxyphenyl)benzamide melting at 104°–106° C.,
N,N-diethyl-4-(1,1,1,2,2-pentafluoroethyl)-2 -(3,4-dimethoxyphenyl)benzamide melting at 94° C.

Example 7

N,N-diethyl-4-trifluoromethyl-2-hydroxy-6 -(3,4-dimethoxyphenyl)benzamide 28.0 g (0.095 mol) of 4-chloro-4-(3,4-dimethoxyphenyl)-1,1,1-trifluoro-3-buten-2-one and 100 ml of anhydrous ethanol are introduced into a 150 ml round-bottomed flask and 18.0 g (0.115 mol) of diethyl acetoacetamide are then rapidly run in. A total of 33.4 g (0.11 mol) of barium hydroxide hydrate Ba(OH$_2$).8H$_2$O are then added in five portions at 2-hourly intervals and with constant stirring. After stirring overnight, the reaction mixture is slowly brought to reflux and then maintained at this temperature for 12 hours. The reaction mixture is acidified with hydrochloric acid, extracted with 3 times 250 ml of ethyl ether and rinsed with water. The organic phase is next extracted with 3 times 100 ml of 3N sodium hydroxide, the organic phase is discarded, the aqueous phase is extracted with twice 200 ml of diethyl ether, filtered through Supercel and then acidified with hydrochloric acid; the product formed is extracted with 3 times 250 ml of dichloromethane to give 32 g (85%) of a beige solid melting at 161° C.

The following derivatives were obtained in the same way:
N-ethyl-N-methyl-4-trifluoromethyl-2-hydroxy-6-(3,4-dimethoxyphenyl)benzamide melting at 114° C.,
1-(4-morpholino)carbonyl-4-trifluoromethyl-2 -hydroxy-6-(3,4-dimethoxyphenyl)benzene melting at 231° C.,
N,N-dimethyl-4-trifluoromethyl-2-hydroxy-6-(3,4-dimethoxyphenyl)benzamide melting at 129° C.

Example 8

N,N-diethyl-4-trifluoromethyl-2-trifluoromethylsulphonato-6-(3,4-dimethoxyphenyl)benzamide To a mixture of 1.0 g (2.6 mmol) of N,N-diethyl-4-trifluoromethyl-2-hydroxy-6-(3,4-dimethoxyphenyl)benzamide above and 1.5 ml of triethylamine (11.6 ml) in 5 ml of dichloromethane at 0° C. is added dropwise 0.5 ml (3 mmol) of trifluoromethanesulphonic anhydride. After a few minutes the reaction has finished: the mixture is extracted with diethyl ether, washed with water, the solvent is evaporated and the product is crystallized from hexane to give 0.8 g (57%) of product melting at 122° C.

Example 9

N,N-diethyl-4-trifluoromethyl-2-(3,4-dimethoxyphenyl)benzamide 0.73 g (1.4 mmol) of the triflate prepared above, 1.4 ml of n-tributylamine, 87 mg (0.21 mmol) of DPPP, 52 mg (0.074 mmol) of Pd(Ph$_3$P)$_2$Cl$_2$, 4.2 ml of DMF and 0.14 ml (3.7 mmol) of formic acid are placed in a round-bottomed flask under argon. The mixture is heated to 110° C. for one hour. After cooling, the mixture is extracted with ether and washed with water to obtain 0.7 g of a mixture of expected product and N,N-diethyl-4 -trifluoromethyl-2-hydroxy-6-(3, 4-dimethoxyphenyl)benzamide. The desired product is selectively extracted with ether in basic medium. After washing with water and evaporation of the solvent under vacuum, 0.34 g (66%) of expected product melting at 108°–110° C. are obtained.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A process for the preparation of a phenylbenzamide derivative of the formula

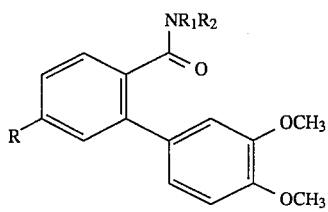

wherein R is alkyl having 1 or 2 carbon atoms substituted with 2 to 5 fluorine atoms, and each of $R_1$ and $R_2$, which can be identical or different, is methyl or ethyl, or $R_1$ and $R_2$ together with the adjacent nitrogen atom form a morpholino radical, said process comprising condensing a haloenone of the formula

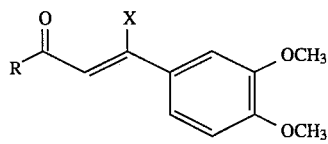

wherein R is defined as above and X is a halogen atom, with an acetoamide of the formula

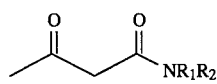

wherein $R_1$ and $R_2$ are defined as above, in the presence of an organic solvent and a stoichiometric amount of one equivalent of base, to afford the corresponding compound of the formula

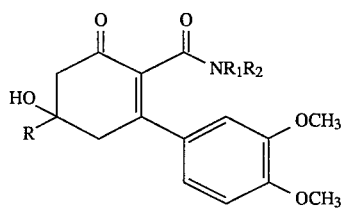

wherein R, $R_1$ and $R_2$ are defined as above; followed by reducing the resultant compound of formula (Z1) in the presence of a reducing agent in a solvent medium, to afford the corresponding compound of the formula

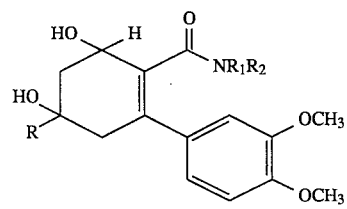

wherein R, $R_1$ and $R_2$ are defined as above; followed by aromatizing the resultant compound of formula (III) by heating to a temperature between about 50° and about 120° C., in an anhydrous solvent medium, in the presence of traces of strong acid, to afford the corresponding compound of formula (A).

2. The process according to claim 1, comprising reducing the compound of formula (Z1) in the presence of a mixed hydride of an alkali metal as the reducing agent.

3. The process according to claim 1, comprising reducing the compound of formula (Z1) in an aliphatic alcohol, an aliphatic ether or a mixture of two or more solvents selected from the group consisting of aliphatic alcohols and aliphatic ethers.

4. The process according to claim 1, comprising aromatizing the compound of formula (III) in an aromatic solvent.

5. The process according to claim 1, comprising aromatizing the compound of formula (III) in the presence of traces of sulphuric acid or para-toluenesulphonic acid.

6. A process for the preparation of a phenylbenzamide derivative of the formula

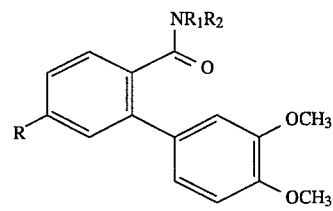

wherein R is alkyl having 1 or 2 carbon atoms substituted with 2 to 5 fluorine atoms, and each of $R_1$ and $R_2$, which can be identical or different, is methyl or ethyl, or $R_1$ and $R_2$ together with the adjacent nitrogen atom form a morpholino radical, said process comprising condensing a haloenone of the formula

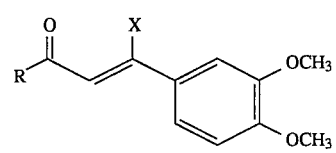

wherein R is defined as above and X is a halogen atom, with an acetoamide of the formula

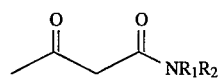

wherein $R_1$ and $R_2$ are defined as above, in the presence of an organic solvent and two equivalents of base, to afford the corresponding compound of the formula

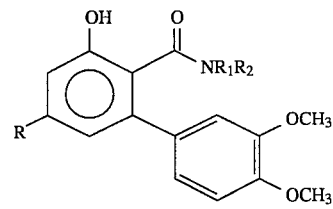

wherein R, $R_1$ and $R_2$ are defined as above; followed by activating the resultant compound of formula (Z2) with an activating agent, to afford the corresponding compound of the formula

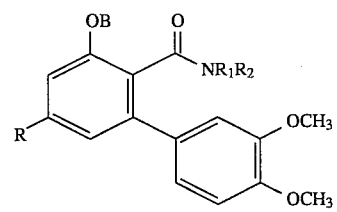

wherein R, $R_1$ and $R_2$ are defined as above and B is the labile portion of the activating agent; followed by reducing the resultant compound of formula (IV) with hydrogen gas in the presence of a conventional hydrogenation catalyst.

7. The process according to claim 6, wherein the activating agent comprises cyanuric chloride, 5-chloro-2-phenyltetrazole, an optionally halogenated alkylsulphonyl chloride or anhydride, saccharin chloride or sulphur trioxide.

* * * * *